United States Patent [19]

Takeda et al.

[11] Patent Number: 4,475,394

[45] Date of Patent: Oct. 9, 1984

[54] ULTRASONIC METHOD OF DETERMINING NATURE OF FLAWS BY INCREMENTAL SCANNING

[75] Inventors: Hiroyuki Takeda, Hiroshima; Kunio Kudo, Sendai; Izumi Kobayashi, Higashikurume; Yohsuke Ojiri, Kasugai; Mitsuyuki Oda, Tokyo; Sakae Sugiyama, Tohkai, all of Japan

[73] Assignee: Hitachi, Ltd., Tokyo, Japan

[21] Appl. No.: 340,718

[22] Filed: Jan. 19, 1982

[30] Foreign Application Priority Data

Jan. 19, 1981 [JP] Japan ................................ 56-6317

[51] Int. Cl.³ ........................................... G01N 29/04
[52] U.S. Cl. ..................................... 73/598; 73/600; 73/602; 73/621; 73/629; 73/633
[58] Field of Search ................. 73/602, 600, 598, 620, 73/621, 629, 633

[56] References Cited

U.S. PATENT DOCUMENTS

| | | | |
|---|---|---|---|
| 3,885,224 | 5/1975 | Klahr | 73/602 |
| 3,996,792 | 12/1976 | Kubota et al. | 73/621 |
| 4,206,654 | 6/1980 | Keller et al. | 73/620 |
| 4,228,804 | 10/1980 | Holasek et al. | 73/602 |
| 4,317,370 | 3/1982 | Glenn | 73/620 |

*Primary Examiner*—Howard A. Birmiel
*Attorney, Agent, or Firm*—Beall Law Offices

[57] ABSTRACT

In ultrasonic flaw inspection for determining the size of a flaw by emitting an ultrasonic wave to a subject via a probe and receiving an ultrasonic echo from said flaw existing inside said subject, changes in the propagation distances of the ultrasonic echoes before and after movement of said probe through a micro-small distance are compared with each other and the ultrasonic echoes are determined to result from the same flaw if the change width falls within a predetermined value determined by the angle of incidence of the ultrasonic wave and the directional angle.

18 Claims, 13 Drawing Figures

| | |
|---|---|
| $x_i$ | $y$ |
| $t_1, i$ | |
| $p_1, i$ | |
| $x_{i+1}$ | $y$ |
| $t_2, i+1$ | |
| $p_2, i+1$ | |
| $t_1, i+1$ | |
| $p_1, i+1$ | |
| ⋮ | ⋮ |
| $x_{i+m}$ | $y$ |
| $t_2, i+m$ | |
| $p_2, i+m$ | |
| $t_1, i+m$ | |
| $p_1, i+m$ | |
| $x_{i+m+1}$ | $y$ |
| $t_1, i+m+1$ | |
| $p_1, i+m+1$ | |

FIG. 12

ULTRASONIC METHOD OF DETERMINING NATURE OF FLAWS BY INCREMENTAL SCANNING

BACKGROUND OF THE INVENTION

This invention relates to a method of determining an ultrasonic echo and also to an apparatus practicing the method. More particularly, the present invention relates to a method of determining an ultrasonic echo specifically suited for use when a plurality of flaws to be detected exist adjaceent one another, and to a apparatus to be used for practicing such a method.

In ultrasonic flaw inspection, it is essentially necessary not only to detect a flaw or flaws of a subject such as a structure or an instrument but also to accurately determine the size of the flaw. To determine the size of a flaw in a subject, there has been known a method in which an ultrasonic probe (hereinafter referred to as the "probe") is linearly scanned on the subject to observe an ultrasonic echo from the subject and calculate the size of the flaw from the probe scanning distance within a range in which the echo amplitude exceeds a predetermined value. The principle of this method will be explained with reference to FIGS. 1 through 7.

Figure 1:
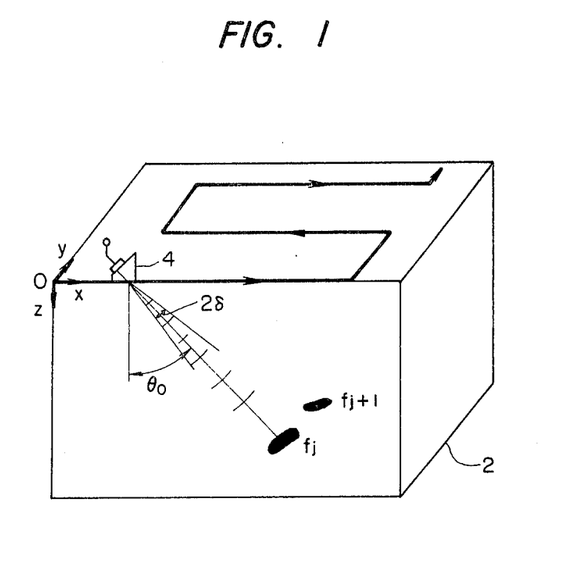
FIG. 1 is a schematic view useful for explaining scanning in ultrasonic flow inspection.

FIG. 1 schematically represents the method of scanning in the ultrasonic flaw inspection. Two flaws $f_j$ and $f_{j+1}$ exist on the subject 2. To determine the sizes of these flaws $f_j$ and $f_{j+1}$, the ultrasonic wave is emitted from the ultrasonic probe 4 to the subject 2 with an angle of incidence $\theta_o$. To receive the reflected ultrasonic echo from the flaw in the subject 2 or a reflecting body such as a boundary of a shape, the probe 4 is linearly scanned on a line as indicated by an arrow on the block in FIG. 1. Now, the methods of detecting only one flaw $f_j$, and detecting both flaws $f_j$ and $f_{j+1}$ will be described, respectively.

Figure 2:
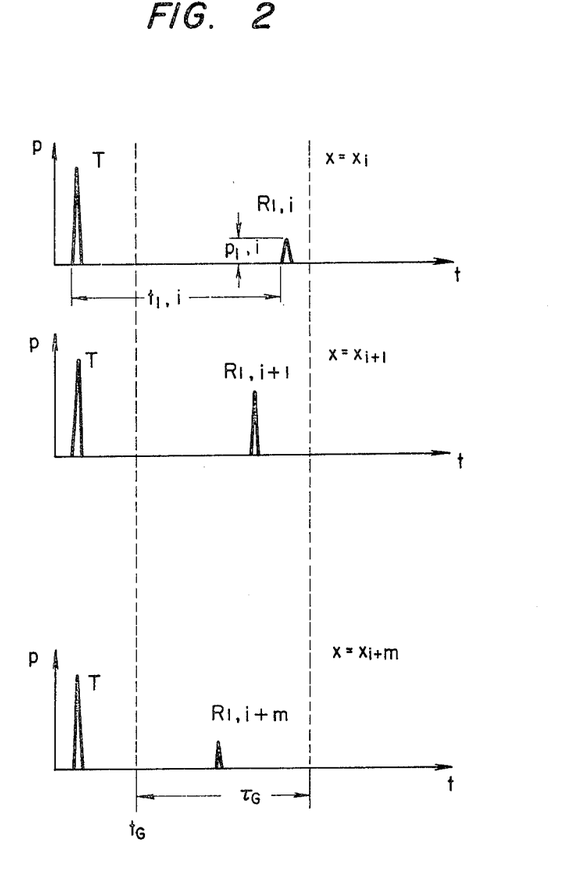
FIG. 2 is a waveform diagram of the ultrasonic echoes obtained by scanning in FIG. 1 when there is only one flaw.
Figure 3:
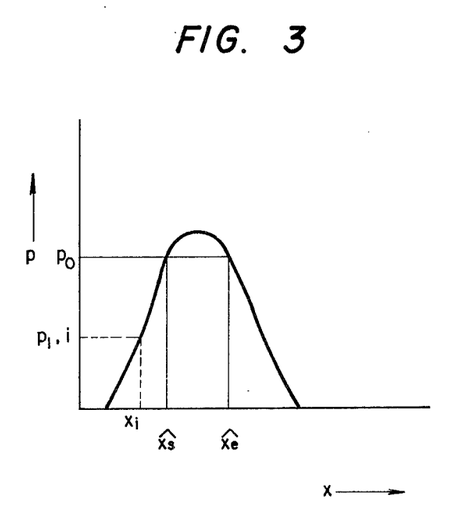
FIG. 3 is a diagram showing the change in the ultrasonic echo amplitude with respect to the probe scanning positions of FIG. 1.
Figure 4:
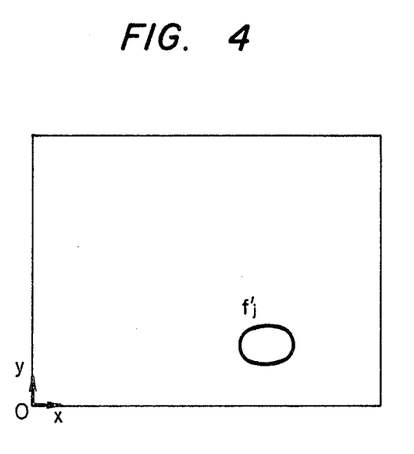
FIG. 4 shows an ultrasonic image of the flaw, obtained by plotting the change in the ultrasonic echo amplitude shown in FIG. 3.

First, the method of detecting only one flaw will be described. This corresponds to a case in which a plurality of flaws are far away from one another, for example. Since the probe 4 has a directional angle $\delta$, it receives ultrasonic echoes $R_{1,i}, R_{1,i+1}, \ldots R_{1,i+m}$ such as shown in FIG. 2 for one flaw $f_j$ due to its linear scanning. Here, the notation $R_{1,i}$ represents one echo that is received by the probe at a probe position $x_i$. Symbols $t_{1,i}$ and $p_{1,i}$ in FIG. 2 represent the echo propagation time and amplitude, respectively, and T represents the incident wave. As shown in FIG. 3, when the probe 4 is made to scan at $x_i, x_{i+1}, \ldots x_{i+m}$, the ultrasonic echoes $R_{1,i}, R_{1,i+1}, \ldots R_{1,i+m}$ are received. In the interim, the echo amplitude P and the echo propagation time t also change as the distance between the probe 4 and the flaw $f_j$ changes. The size of the flaw $f_j$ on the X axis can be estimated from the echo appearing within a predetermined time gate (start time $t_G$, width $\tau_G$) in FIG. 2 in the following way. First, the echo amplitude P with respect to the probe position x is plotted. The scanning range $\hat{x}_s$–$\hat{x}_e$ of the probe position x in which the echo amplitude P exceeds a predetermined value $p_o$ is then determined. The size of this range represents the flaw size. Those echoes whose amplitude is smaller than the predetermined value $P_o$ are regarded as noise signals and are not considered. The results of linear scanning on the subject obtained in this way are plotted on a plane as shown in FIG. 4. In FIG. 4, the ultrasonic image of the flaw $f_j$ is represented by $f_j'$.

The conventional method would be free from any problem if only one echo appears within the time gate, that is, if only one flaw exists in the subject or even though a plurality of flaws are present, if they are so far away from one another as to be beyond the range of directional angle $\delta$. However, such a case is rare indeed and echoes from a plurality of flaws or boundary echoes having the subject shape are obtained in practice. For these reasons, it has been difficult to accurately determine the size of a flaw by the conventional method.

Figure 5:
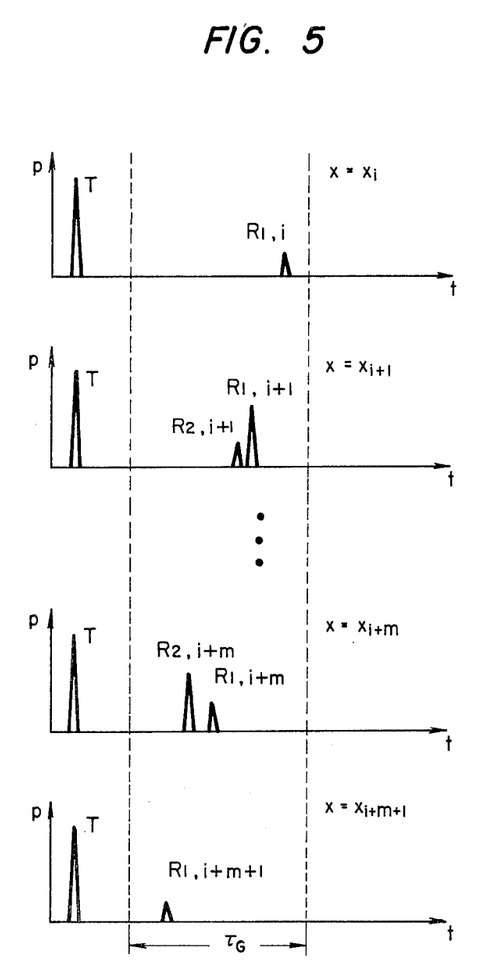
FIG. 5 is a waveform diagram of the ultrasonic echoes when two flaws exist.
Figure 6:
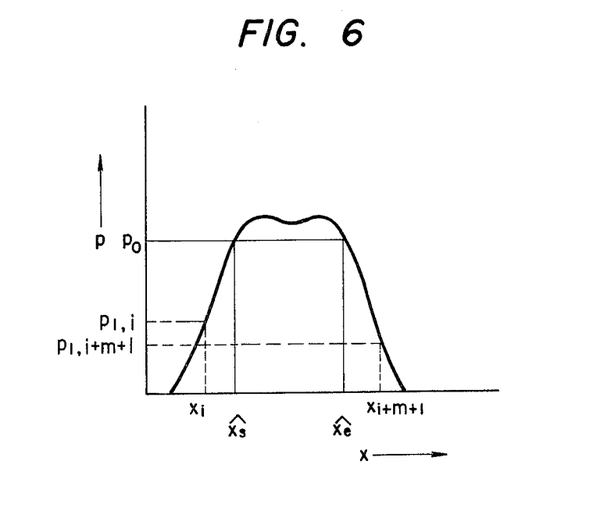
FIG. 6 is a diagram showing the change in the ultrasonic echo amplitude corresponding to the probe positions when two flaws exist.
Figure 7:
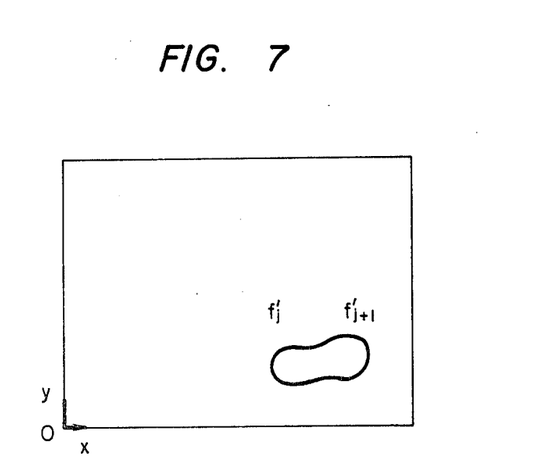
FIG. 7 shows an ultrasonic image of the flaw obtained by plotting the change in the ultrasonic echo amplitude shown in FIG. 6.

Next, the method of flaw inspection when two flaws $f_j$ and $f_{j+1}$ are present adjacent to each other as shown in FIG. 1 will be described. When the probe 4 is permitted to linearly scan in the same way as in the flaw inspection of only one flaw $f_j$, ultrasonic echoes $R_{1,i}, R_{1,i+1}, \ldots R_{1,i+m+1}$ and $R_{2,i+1}, \ldots R_{2,i+m}$ are observed as shown in FIG. 5. FIG. 6 represents a maximum value envelope in which the maximum value of the echo amplitude P and the probe position x within a predetermined gate time $\tau_G$ correspond to each other. It is obtained by plotting the maximum values of the echo amplitude P at the probe positions x when the probe is permitted to scan in the direction of the X axis. In the maximum value envelope of FIG. 6, the scanning range $\hat{x}_s$–$\hat{x}_e$ within which the echo amplitude P exceeds a certain predetermined value $p_o$ is obtained and the same procedures are carried out for all the scanning lines of FIG. 1. The result is shown in FIG. 7. As can be seen clearly from FIG. 7, the ultrasonic images $f_j'$ and $f_{j+1}'$ are not separated from each other but are represented as one flaw. This is because the amplitude P shown in FIG. 6 is described by plotting the maximum value of the amplitude, though the echoes $R_{1,i}, R_{1,i+1}, \ldots R_{1,i+m}$ from the flaw $f_j$ and the echoes $R_{2,i+1}, \ldots R_{2,i+m+1}$ from the flaw $f_{j+1}$ simultaneously as they appear within the time gate $\tau_G$.

As described above, the conventional method has the drawback that when a plurality of flaws exist close to one another within the range of the directional angle of the probe, mistakes in determination occurs as if one large flaw is present and hence, the size of each flaw can not be detected accurately.

SUMMARY OF THE INVENTION

In carrying out ultrasonic flaw inspection for a subject in which a plurality of flaws exist close to one another, the present invention is directed to provide a method of accurately determining the sizes of the flaws by classifying each received ultrasonic echo according to the flaw that generates the echo. The present invention is also directed to provide an apparatus for practising such a method.

The present invention is characterized in that changes in signals corresponding to ultrasonic echoes before and after movement of the probe through a micro-small distance are compared with each other and when the change width falls within a predetermined value determined on the basis of the angle of incidence and directional angle of the probe, the ultrasonic echoes are determined as those from the same flaw.

DESCRIPTION OF THE PREFERRED EMBODIMENTS

Figure 8:
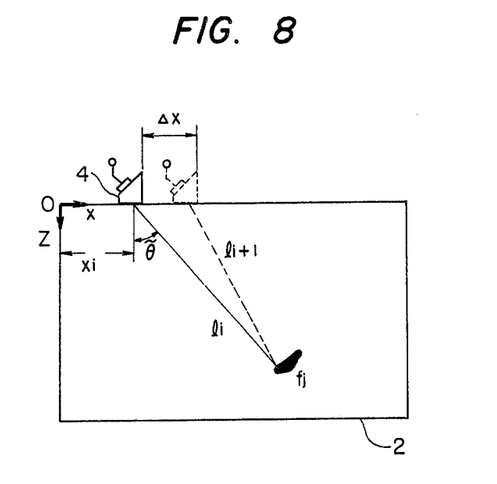
FIG. 8 is a schematic view useful for explaining the principle of the present invention.

The principle of the present invention will be described with reference to FIG. 8, which represents the case in which the subject 2 having the flaw $f_j$ is subjected to ultrasonic flaw inspection using an emerging angle probe 4.

On the x-z plane of the subject 2, the probe 4 receives an ultrasonic echo from the flaw $f_j$ before being moved (position $x_i$). The propagation distance $l_1$ of the ultrasonic echo can be obtained from the propagation time. In this case, the angle $\tilde{\theta}$ (symbol ~ is attached because it does not represent an accurate angle due to directivity) of the ultrasonic wave striking the flaw $f_j$ falls within the range of from $(\theta_o - \delta)$ to $(\theta + \delta)$ because the probe has directivity. When the probe 4 is moved a micro-small distance $\Delta x$, an ultrasonic echo having a propagation distance $l_{i+1}$ from the flaw $f_j$ is received. If the position of the flaw $f_j$ on the x-z plane is expressed as (X, Z), the following equations (1) through (3) can be established:

$$X = x_i + l_i \sin\theta \tag{1}$$

$$Z = l_i \cos\theta \tag{2}$$

$$l_{i+1} = \{Z^2 + (X - x_i - \Delta x)^2\}^{\frac{1}{2}} \tag{3}$$

From equations (1) through (3), the difference of the echo propagation distance, $\Delta l_i$, can be derived by the following equation (4):

$$\frac{|\Delta l_i|}{l_i} = |\frac{1}{2}\left(\frac{\Delta x}{l_i}\right)^2 - \left(\frac{\Delta x}{l_i}\right)\sin\theta| \text{ an absolute value line} \tag{4}$$

where $$\Delta l_i = l_{i+1} - l_i \tag{5}$$

The difference of the propagation distance $\Delta l_i$ and the probe moving distance $\Delta x$ are normalized by the propagation distance $l_i$ of the echo received before movement of the probe:

$$S = \frac{|\Delta l_i|}{l_i} \tag{6}$$

$$q = \frac{\Delta x}{l_i} \tag{7}$$

Figure 9:
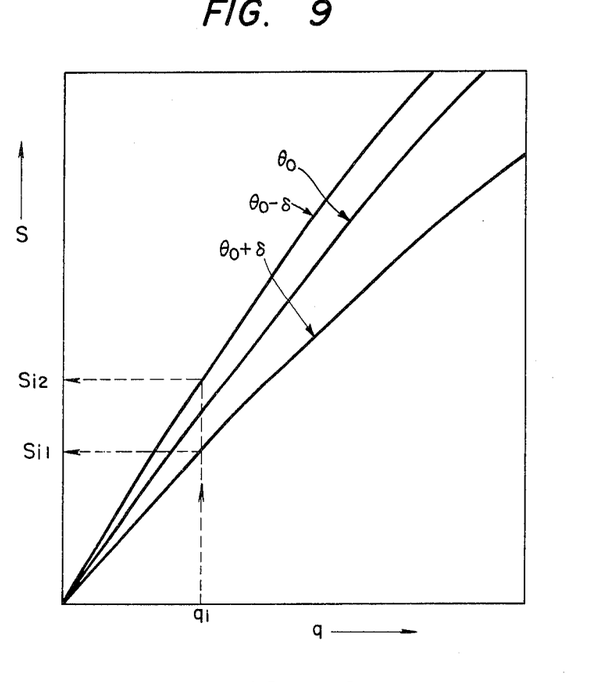
FIG. 9 is a diagram showing the propagation distance change characteristic with respect to the moving distance of the probe for each angle of incidence of the ultrasonic wave.

FIG. 9 shows the propagation distance characteristics of the echo with respect to the probe moving distance characteristic. Since the propagation distance $l_i$ can be obtained within the range of the angle $\theta$ of incidence of the ultrasonic wave from $(\theta - \delta)$ to $(\theta + \delta)$, FIG. 9 shows this angle of incidence $\theta$ as a parameter. According to FIG. 9, that is, equation (4), it can be understood that when the moving distance characteristic of the probe is $q_i$, the change in the echo propagation distance characteristic after movement falls within the range of $S_{i1}$ to $S_{i2}$.

In a realistic case in which the moving distance characteristic q of the probe is small such as the probe moving distance $\Delta x \leq 4$ mm or $q \leq 0.2$ when $l_i \geq 20$ mm, the change S in the propagation distance characteristic in FIG. 9 becomes 0.1 to 0.15 when the angle of incidence $\theta_o = 45°$ and the directional angle $\delta = 10°$. Hence, the following approximate expression (8) may be used in place of equation (4):

$$k_1 q \leq S \leq k_2 q \tag{8}$$

Here, constants $k_1$ and $k_2$ are determined by the directional angle $\delta$ of the probe and the angle of incidence $\theta_o$ (generally, $\theta_o = 45°$ and $\delta = 10°$). In the abovementioned embodiment, the constants $k_1$ and $k_2$ are 0.5 and 0.75, respectively. These constant $k_1$ and $k_2$ can be obtained by linearly approximating the chart of FIG. 9.

When the principle described above is applied to the waveform situations shown in FIG. 5, the echo $R_{1,i}$ at the probe position $x_i$ becomes $R_{1,i+1}$ when the probe moves to the position $x_{i+1}$ as the propagation distance changes. This can be distinguished from the other echo $R_{2,i+1}$. When the probe is further moved, the next echo $R_{1,i+m}$ appears within the range of the propagation distance S that is determined by this moving distance q. In this manner, by sequentially tracing the echoes, the ultrasonic echoes can be determined in such a manner that the echoes $R_{1,i} \ldots R_{1,i+m}$ result from the flaw $f_j$, the echoes $R_{2,i+1} \ldots R_{1,i+m+1}$ result from the flaw $f_{j+1}$, and so forth can be correlated to their different flaw sources respectively.

The foregoing explains the case in which the probe is permitted to scan on a line of the X axis, but the same concept can also be applied to determination of the echoes with respect to the probe position (x, y) and probe position (x, y+$\Delta$y) on the x-y plane. When the ultrasonic wave is projected onto the y-z plane, the angle of incidence $\theta$ of the ultrasonic wave enters the range of the directional angle of the probe from $-\delta$ to $\delta$. Echo determination on the adjacent scanning lines can be made from the equation (9) by making use of the relation $(-\delta) \leq \tilde{\theta} \leq \delta$ in place of the relation $(\theta_o - \delta) \leq \tilde{\theta} \leq (\theta_o + \delta)$, so that in the case of the x-z plane:

$$k_3 q \leq S \leq k_4 q \tag{9}$$

The constants $k_3$ and $k_4$ are determined by the directional angle $\delta$ of the probe.

In accordance with the present invention as described above, the number of maximum value envelopes drawn, representing the relation between the probe position and the echo amplitude, will correspond to the number of flaws, and the sizes of flaws adjacent to one another can be accurately detected.

Figure 10:
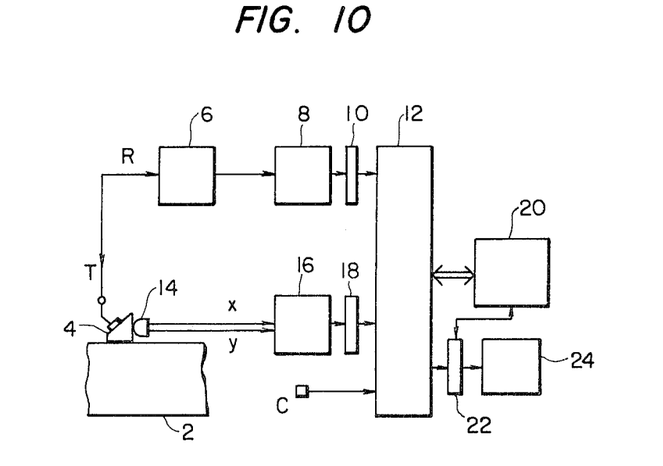
FIG. 10 is a block diagram showing an embodiment of the present invention.

FIG. 10 is a block diagram of the embodiment of the present invention.

A pulse wave T is applied to the probe 4 for detecting the flaws of the subject 2 from an ultrasonic transmitter-receiver 6 with a predetermined interval and the ultrasonic echo R reflected from the flaw inside the subject 2 is applied to the receiver portion of the ultrasonic transmitter-receiver 6, thereby effecting predetermined amplification. Since this amplified signal is an analog signal, it is converted into a digital signal by an A/D convertor 8 and is then stored in a memory 12 via an input controller 10. On the other hand, the probe positions in x and y directions are picked up by a probe position detector 14 and are converted into digital signals by an A/D convertor 16. The digital signals are stored in memory 12 via air input controller 18. The probe position detector 14 consists of potentiometers or photoelectronic elements and position signals are produced in an interlocking arrangement with the operation of an automatic scanner of the probe 4 or the like. Various constants such as the angle of incidence $\theta_o$ of the probe 4, its directional angle $\delta$, the sound velocity v determined by the material of the subject 2, the aforementioned predetermined value $p_o$ and the like are set to the memory 12 as set values for calculation from C. The memory 12 is connected to a calculator 20 to perform various calculations and control the unit. The results of the calculations are displayed on a display 24 via an output controller 22.

Figure 11:
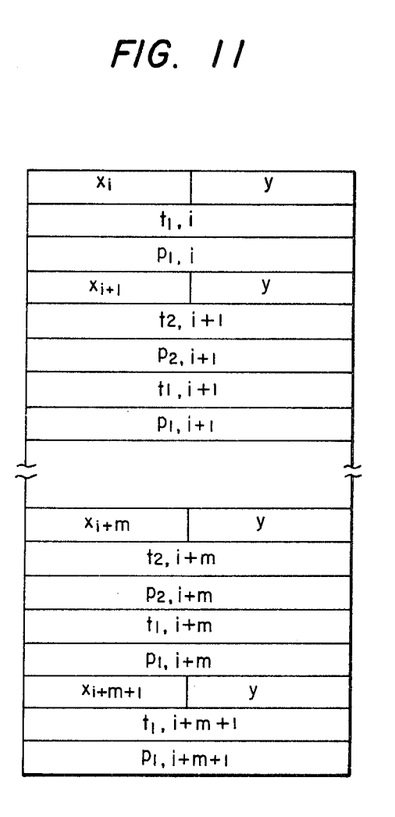
FIG. 11 is a data table distribution chart for practicing the present invention.

Inside memory 12, the propagation time t and amplitude p of the echoes obtained from the probe positions (x, y) are arranged in order in table form, and FIG. 11 shows a data table for the waveform situation shown in FIG. 5, for example. (However, only one stroke in the x direction is shown in the table). The calculator 20 properly withdraws the memory content and performs calculations in accordance with the flow chart shown in FIG. 12.

Figure 12:
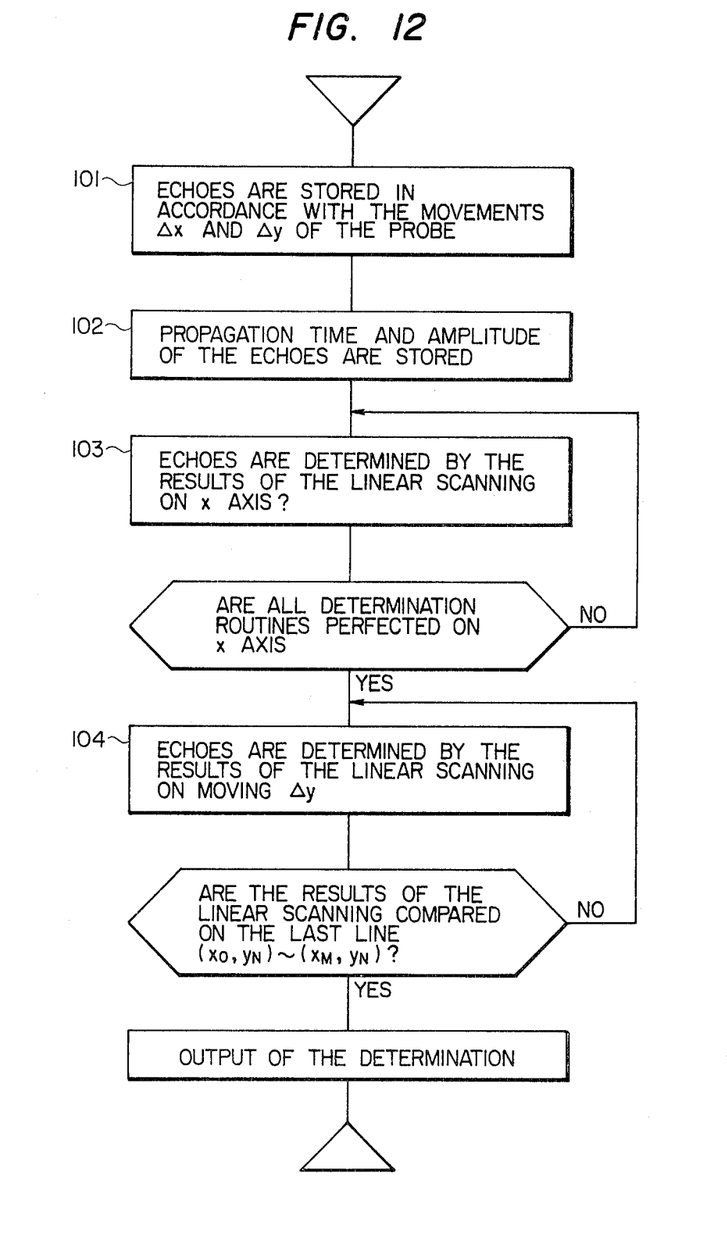
FIG. 12 is an operation flow chart for practising the present invention.

In FIG. 12, steps 101 and 102 represent the process in which the position detection signals are stored in the memory 12 and step 103 represents the process in which the calculator 20 calculates and determines whether the contents of the equation (4) or the content in FIG. 9 within the range of $(\theta_o-\delta)\leq\theta\leq(\theta_o+\delta)$. Step 104 represents the process in which calculation is made within the range of $-\delta\leq\theta\leq\delta$ in the y direction.

Figure 13:
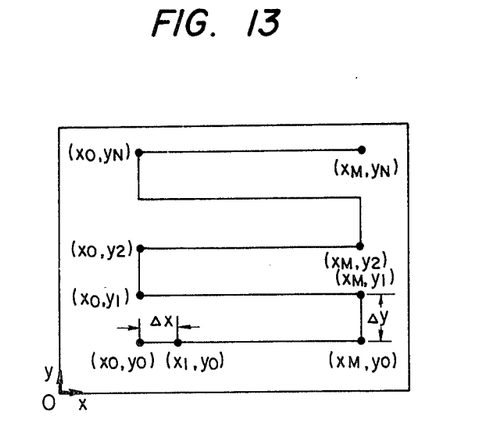
FIG. 13 is a diagram showing the determination routines in accordance with the present invention.

The calculation in FIG. 12 will be described with reference to the scanning chart of FIG. 13. Scanning of the probe starts from the position $(x_o, y_o)$ and ends up with the position $(x_M, y_N)$. Whenever the probe 4 moves through distances $\Delta x$ and $\Delta y$ on the x and y axes, respectively, the ultrasonic echoes are stored in the memory 12 and their propagation time and amplitude are memorized. Determination of a large number of ultrasonic echoes is independently carried out by linear scanning of the portion between $(x_o, y_o)$ and $(x_M, y_o)$, the portion between $(x_o, y_1)$ and $(x_M, y_1)$, ..., and the portion between $(x_o, y_N)$ and $(x_M, y_N)$. Next, the results of linear scanning adjacent to one another, i.e., $(x_o, y_o) \sim (x_M, y_o)$ and $(x_o, y_1) \sim (x_M, y_1)$, $(x_o, y_1) \sim (x_M, y_1)$ and $(x_o, y_2) \sim (x_M, y_2)$, ..., $(x_o, y_{N-1}) \sim (x_M, y_{N-1})$ and $(x_o, y_N) \sim (x_M, y_N)$, are sequentially compared for determination. When all determination routines are perfected, the result is output to the display 24 shown in FIG. 10. As the system of this output, the maximum value envelope shown in FIG. 3, the ultrasonic image of the flaw shown in FIG. 4, the ultrasonic image in the x-z section, the ultrasonic image in the y-z section, and the like, can easily be produced as the output.

As described in the foregoing, the present invention determines whether or not a large number of ultrasonic echoes obtained by scanning the probe results from the same flaw and separately provides the maximum value envelope for each flaw. Hence, the present invention makes it possible to accurately determine the size of the flaw and thus to improve strength calculation for plant structures and instruments as well as quality control of the materials.

What is claimed is:

1. In ultrasonic flaw inspection for determining the size of a flaw by emitting an ultrasonic wave to a subject via a probe and receiving an ultrasonic echo from said existing flaw inside said subject, a method of determining the ultrasonic echo characterized in that changes in characteristics of signals corresponding to the ultrasonic echoes before and after incremental movements of said probe along a scanning path are compared with each other and the ultrasonic echoes are determined to result from the same flaw if the changes fall within a range determined by the angle of incidence $\theta$, of the ultrasonic wave and directional angle $\delta$, of the ultrasonic wave.

2. The method of determining the ultrasonic echo as defined in claim 1 wherein said characteristics of said signals corresponding to the ultrasonic echoes are indicative of the propagation distances of the echoes.

3. The method of determining the ultrasonic echo as defined in claim 1 wherein said characteristics of said signals corresponding to the ultrasonic echo are the propagation times of the echoes.

4. In ultrasonic flaw inspection for determining the size of a flaw by emitting an ultrasonic wave to a subject via a probe and receiving an ultrasonic echo from said flaw existing inside said subject, an apparatus for determining the ultrasonic echo, comprising:
a memory portion for storing signals corresponding to a plurality of ultrasonic echoes obtained by scanning said probe, position signals of said probe and constants relating to said subject and said probe;
a calculation portion for comparatively calculating changes in characteristics of said signals corresponding to the ultrasonic echoes before and after incremental movement of said probe along a scanning path, on the basis of the memory content of said memory portion; and
a display for displaying results from said calculation portion.

5. The apparatus for determining the ultrasonic echo as defined in claim 4 wherein said memory portion stores the angle of incidence $\theta$, of the ultrasonic wave and the directional angle $\delta$, of said wave as said constants and said calculation portion calculates comparatively said changes in said characteristics of said signals corresponding to the ultrasonic echoes and a value determined by the angle of incidence and the directional angle of said ultrasonic wave.

6. The apparatus for determining the ultrasonic echo as defined in claims 4 or 5 wherein said characteristics of said signals corresponding to the ultrasonic echoes are the propagation distances of the echoes.

7. The apparatus for determining the ultrasonic echo as defined in claims 4 or 5 wherein said characteristics of said signals corresponding to the ultrasonic echoes are the propagation times of the echoes.

8. In ultrasonic flaw inspection for determining the size of a flaw by emitting an ultrasonic wave to a subject via a probe and receiving an ultrasonic echo from said flaw existing inside said subject, an apparatus for determining the ultrasonic echo, comprising:
- a memory portion for storing a plurality of ultrasonic echo signals obtained by scanning said probe, the angle of incidence $\theta$, the directional angle $\delta$ of the ultrasonic wave and a range determined by reference to the angle of incidence and the directional angle of said ultrasonic wave;
- a calculation portion for comparatively calculating relative to said range, changes in characteristics of the ultrasonic echo signals before and after movement of said probe; and
- a display for producing a result of calculation by said calculation portion as output and displaying the output so that the ultrasonic echoes are displayed as originating from the same flaw when a signal change falls within said range and are displayed as originating from different flaws when the signal change falls outside said range.

9. An ultrasonic flaw inspection device for determining the size of and distinguishing between a plurality of flaws in a subject by emitting an ultrasonic wave to the subject via a probe and receiving an ultrasonic wave to the subject via a probe and receiving an ultrasonic echo from each of the flaws existing inside the subject, comprising;
- ultrasonic probe means for passing a single sonic wave into the subject at a fixed angle of incidence $\theta$, and within a fixed directional angle $\delta$;
- means for moving the probe along a scanning path relative to the subject;
- means for measuring incremental movements of said probe along said path and producing corresponding probe movement signals;
- means carried by said probe receiving the ultrasonic echo of said ultrasonic wave from each flaw within the subject along the path of the ultrasonic wave and producing an echo characteristic signal;
- means for determining the distance between said probe and a flaw within the subject for each echo and for producing corresponding propagation distance signals;
- means comparing the change in said propagation distance signals with the change in said probe movement signals for two successive echoes according to a fixed relationship, and storing the second of two characteristic signals as selectively corresponding to either the same flaw or a different flaw than the flaw producing the preceding first echo, in accordance with said comparison; and
- means separately displaying flaw size information for the first flaw and the flaw size information for the second flaw in accordance with said separately stored echo characteristic signals.

10. The apparatus according to claim 9, wherein said means for measuring produces incremental movement for the period of time between successively received echoes and produces corresponding digital signals.

11. The apparatus according to claim 9, wherein said means for determining distance between the probe and the flaw producing a specific echo measures the time between the transmission of the ultrasonic wave from said probe and the reception of the echo of said wave produced by said flaw, and produces a corresponding digital signal.

12. The apparatus according to claim 9, wherein said comparing means compares the probe-to-flaw distance of successive echoes to produce a digital signal corresponding to the difference between said distances, normalizes said difference by dividing said difference between said distances by the distance of one of said echoes and normalizes the difference between movement signals for adjacent echoes by dividing the difference between said movement signals by said distance of said one of said echoes.

13. The apparatus according to claim 12, wherein said comparing means compares the normalized probe movement signal difference with the normalized propagation distance signal difference for the successive echoes using a relation dependent upon the angle of incidence and directional angle of the ultrasonic wave so that if said comparison falls within a range, the adjacent echoes are determined to be from the same flaw and if said comparison falls outside of said range, the successive echoes are determined to be from different flaws.

14. An ultrasonic flaw inspection method for determining the size of and distinguishing between a plurality of flaws in a subject by emitting an ultrasonic wave to the subject via a probe and receiving an ultrasonic echo from each of the flaws existing inside the subject, comprising the steps of:
- passing a single ultrasonic wave from an ultrasonic probe into the subject at a fixed angle of incidence and with a fixed directional angle;
- moving the probe along a scanning path relative to the subject;
- measuring increments of said probe along said path and producing a corresponding probe movement signal;
- receiving at the probe the ultrasonic echo of said ultrasonic wave from each flaw within the subject that is along the path of the ultrasonic wave and producing an echo characteristic signal;
- determining the distance between said probe and a flaw within the subject for each echo and producing a corresponding propagation distance signal;
- comparing the change in said propagation distance signals with the change in said probe movement signals for two successive echoes according to a fixed relationship, and storing the second of the two characteristic signals as selectively corresponding to either the same flaw as or a different flaw than the flaw producing the preceding first echo, in accordance with a result obtained during said step of comparing; and
- separating displaying flaw size information for the first flaw and flaw size information for the second flaw in accordance with said separately stored echo characteristic signals.

15. The method according to claim 14, wherein said step of measuring produces incremental movement for the period of time between successively received echoes and produces corresponding digital signals.

16. The apparatus according to claim 14, wherein said step of determining the distance between the probe and the flaw producing a specific echo measures the time between the sending of the ultrasonic wave from said probe and the receiving of the echo of said wave produced by said flaw, and produces a corresponding digital signal.

17. The method of claim 16, wherein said step of comparing compares the probe-to-flaw distance of successive echoes to produce a digital signal corresponding to the differences between said distances, normalizes said propagation difference by dividing said propagation difference by the distance, and normalizes the difference between movement signals for successive echoes by dividing the difference between movement signals by said distance.

18. The method of claim 17, wherein said comparing means compares the normalized propagation distance signal difference for successive echoes using a constant dependent upon the angle of incidence and directional angle of the ultrasonic wave so that if said comparison falls within a range, the successive echoes are determined to be from the same flaw and if said comparison falls outside said range, the successive echoes are determined to be from different flaws.

* * * * *